(12) United States Patent
Browning

(10) Patent No.: US 7,226,585 B2
(45) Date of Patent: Jun. 5, 2007

(54) METHOD AND SYSTEM FOR TREATING HAIR

(75) Inventor: Paul T. Browning, Trafalgar, IN (US)

(73) Assignee: Kenra, LLC, Indianapolis, IN (US)

( * ) Notice: Subject to any disclaimer, the term of this patent is extended or adjusted under 35 U.S.C. 154(b) by 542 days.

(21) Appl. No.: 10/735,371

(22) Filed: Dec. 12, 2003

(65) Prior Publication Data

US 2004/0126348 A1 Jul. 1, 2004

Related U.S. Application Data

(63) Continuation of application No. 10/001,422, filed on Nov. 2, 2001, now Pat. No. 6,723,308.

(51) Int. Cl.
- *A61K 8/00* (2006.01)
- *A61K 8/02* (2006.01)
- *A61K 8/72* (2006.01)

(52) U.S. Cl. ............... 424/70.1; 424/70.11; 424/70.2; 424/70.21; 424/401

(58) Field of Classification Search ............... None
See application file for complete search history.

(56) References Cited

U.S. PATENT DOCUMENTS

| | | | |
|---|---|---|---|
| 2,350,178 A | 5/1944 | Martin | |
| 2,418,664 A | 6/1947 | Ramsey | |
| 3,533,417 A | 10/1970 | Twickenham et al. | |
| 3,672,375 A | 6/1972 | Kalopissis et al. | |
| 3,910,289 A | 10/1975 | Wajaroff et al. | |
| 3,912,808 A | 10/1975 | Sokol | |
| 3,971,391 A | 7/1976 | Bore et al. | |
| 3,973,574 A | 8/1976 | Minagawa et al. | |
| 3,996,146 A | 12/1976 | Tarasov et al. | |
| 4,027,008 A | 5/1977 | Sokol | |
| 4,134,411 A | 1/1979 | Yamazaki | |
| 4,175,572 A | 11/1979 | Hsiung et al. | |
| 4,240,450 A | 12/1980 | Grollier et al. | |
| 4,273,760 A | 6/1981 | Koehler et al. | |
| 4,275,748 A | 6/1981 | Graziano | |
| 4,303,085 A | 12/1981 | de la Guardia et al. | |
| 4,304,244 A | 12/1981 | de la Guardia et al. | |
| 4,313,933 A | 2/1982 | Yamazaki | |
| 4,314,572 A * | 2/1982 | de la Guardia et al. .... | 132/204 |
| 4,324,263 A | 4/1982 | de la Guardia | |
| 4,327,751 A | 5/1982 | Evans | |
| 4,349,537 A | 9/1982 | Forbriger, Jr. | |
| 4,361,157 A | 11/1982 | James | |
| 4,373,540 A | 2/1983 | de la Guardia | |
| 4,381,920 A | 5/1983 | Garlen | |
| 4,416,296 A | 11/1983 | Meyers | |
| 4,524,787 A | 6/1985 | Khalil et al. | |
| 4,602,648 A * | 7/1986 | Syed et al. ................. | 132/204 |
| 4,630,621 A | 12/1986 | Pontani | |
| 4,770,872 A | 9/1988 | Hsiung et al. | |
| 4,770,873 A | 9/1988 | Wolfram et al. | |
| 4,772,462 A | 9/1988 | Boothe et al. | |
| 4,781,724 A | 11/1988 | Wajaroff et al. | |
| 4,828,750 A | 5/1989 | Simion et al. | |
| 4,834,971 A | 5/1989 | Klenk et al. | |
| 4,844,886 A | 7/1989 | Hartmann et al. | |
| 4,855,130 A | 8/1989 | Konrad et al. | |
| 4,898,726 A | 2/1990 | Beste | |
| 4,950,485 A | 8/1990 | Akhtar et al. | |
| 4,975,275 A | 12/1990 | Mitamura et al. | |
| 4,982,749 A | 1/1991 | Baker et al. | |
| 4,982,750 A | 1/1991 | Kaitz | |
| 4,992,267 A | 2/1991 | DenBeste et al. | |
| 5,002,761 A * | 3/1991 | Mueller et al. ............ | 424/70.1 |
| 5,068,101 A | 11/1991 | Akhtar et al. | |
| 5,132,107 A | 7/1992 | Lange | |
| 5,148,822 A | 9/1992 | Akhtar | |
| 5,161,553 A | 11/1992 | Cohen et al. | |
| 5,254,336 A | 10/1993 | Hoshowski et al. | |
| 5,293,885 A | 3/1994 | Darkwa et al. | |
| 5,294,230 A | 3/1994 | Wu et al. | |
| 5,376,364 A | 12/1994 | Darkwa et al. | |
| 5,503,826 A | 4/1996 | Lang et al. | |
| 5,520,909 A | 5/1996 | Salce et al. | |
| 5,562,110 A | 10/1996 | Ottenbrite et al. | |
| 5,570,708 A * | 11/1996 | Samain ...................... | 132/205 |
| 5,609,859 A | 3/1997 | Cowsar | |
| 5,635,170 A | 6/1997 | Lang et al. | |
| 5,679,327 A | 10/1997 | Darkwa et al. | |
| 5,989,533 A | 11/1999 | Deegan et al. | |
| 6,110,450 A | 8/2000 | Bergmann | |
| 6,125,856 A | 10/2000 | Yamashita | |
| 6,723,308 B2 * | 4/2004 | Browning .................. | 424/70.1 |
| 6,805,136 B2 * | 10/2004 | Browning .................. | 132/205 |
| 2003/0033677 A1 * | 2/2003 | Nguyen et al. .............. | 8/405 |

FOREIGN PATENT DOCUMENTS

EP 0083095 7/1983

(Continued)

OTHER PUBLICATIONS

"How Were Permanent Waves for Hair Discovered", *MadSci Network: Chemistry*, pp. 1-3, Sep. 2001 http://www.madsci.org/posts/archives/may98/892764277.Ch.r.html.

(Continued)

*Primary Examiner*—Susan Tran
(74) *Attorney, Agent, or Firm*—Bose McKinney & Evans LLP

(57) ABSTRACT

The present invention includes a hair clarifying composition for removing residue from hair. The composition includes an acid component and an amphoteric surfactant. The present invention further includes a method for using the hair clarifying composition to remove residue from the hair.

31 Claims, No Drawings

FOREIGN PATENT DOCUMENTS

| | | |
|---|---|---|
| EP | 0167866 | 1/1986 |
| EP | 0190834 | 8/1986 |
| EP | 0257256 | 3/1988 |
| EP | 0260716 | 3/1988 |
| EP | 0328816 | 8/1989 |
| GB | 2066864 | 7/1981 |
| GB | 2068031 | 8/1981 |
| GB | 2086443 | 5/1982 |
| GB | 2090303 | 7/1982 |
| GB | 2109832 | 6/1983 |
| GB | 2114616 | 8/1983 |
| GB | 2141454 | 12/1984 |
| GB | 2141454 A * | 12/1984 |
| WO | WO 86/01403 | 3/1986 |
| WO | WO 88/00186 | 1/1988 |
| WO | WO 88/02997 | 5/1988 |
| WO | WO 89/02233 | 3/1989 |

OTHER PUBLICATIONS

Clarifying Treatment Spec. Sheet and Formula, Kenra, LLC, Jun. 1996.

Starch, M., "Silicone for Conditioning Damaged Hair" *Soap/Cosmet/Chem. Specialties*, pp. 34-39 (Apr., 1986).

"Dow Corning © Q2-7225 Conditioning Agent", Technical Bulletin Form. No. 22-956-83. Dow Corning Corporation (1983).

* cited by examiner

METHOD AND SYSTEM FOR TREATING HAIR

RELATED APPLICATION

This application is a continuation of patent application Ser. No. 10/001,422, filed Nov. 2, 2001, now U.S. Pat. No. 6,723,308, titled "Hair Clarifying Treatment", the disclosure of which is expressly incorporated by reference herein.

FIELD OF THE INVENTION

The present invention relates to a method and composition for treating hair subsequent to an alkaline hair treatment, such as a hair straightening treatment or a permanent wave treatment.

BACKGROUND

Hair is chemically straightened through a hair straightening treatment. Hair is chemically altered to produce a wavy appearance through a permanent wave treatment. Both commercial hair straightening treatments and commercial permanent wave treatments include applying an alkaline composition to the hair to disrupt the bonds in the hair fibers, in particular the disulfide bonds. Generally, permanent wave treatments have a pH in the range of 9.0 to 9.5 pH and hair straightening treatments have a pH of greater than 12.0, and typically greater than 13.0.

Commercial hair straightening products and commercial permanent wave products are typically based on an alkaline metal hydroxide, such as calcium hydroxide, barium hydroxide, lithium hydroxide, sodium hydroxide, potassium hydroxide, ammonium hydroxide, or combinations thereof. Other commercial hair straightening products include guanidine hydroxide.

A result of the permanent wave treatments or the hair straightening treatments is that residue of the alkaline composition remains in the hair causing the hair to be dull, stiff, crusty or gritty. For example, when a calcium hydroxide based product is used in a hair straightening treatment calcium deposits are left on the hair. The presence of the calcium deposits causes the hair have a dry and gritty feeling and a dull appearance.

As such a need exists for a hair treatment to improve the feel and appearance of the hair subsequent to a hair straightening treatment or a permanent wave treatment without detrimentally affecting the straightness or waviness of the hair achieved through the straightening treatment or permanent wave treatment, respectively.

SUMMARY OF THE INVENTION

The present invention is a composition and method for treating hair.

In one exemplary embodiment, a method for treating hair comprising the steps of straightening the hair with a hair straightening treatment, allowing the hair to normalize, and clarifying the hair with a hair clarifying treatment to remove a residue of the straightening treatment from the hair. In one variation the hair is allowed to normalize by waiting at least 30 minutes between the completion of the hair straightening treatment and the commencement of the clarifying treatment. In another variation, the hair is allowed to normalize by waiting at least 4 hours between the completion of the hair straightening treatment and the commencement of the clarifying treatment. In a further variation, the hair is allowed to normalize by waiting at least 24 hours between the completion of the hair straightening treatment and the commencement of the clarifying treatment. In a yet further variation, the hair is allowed to normalize by waiting at least 48 hours between the completion of the hair straightening treatment and the commencement of the clarifying treatment.

In another exemplary embodiment, a method for treating hair comprising the steps of straightening the hair with a hair straightening treatment, allowing the hair to normalize, and clarifying the hair with a hair clarifying treatment to remove a residue of the straightening treatment from the hair. In one variation the hair clarifying treatment includes the step of applying a composition to the hair. The composition comprising an aqueous solution including an acid component and an amphoteric surfactant. The acid component, in one variation of the composition, the acid component includes at least one acid selected from the group of citric, salicylic, acetic, malic, and ascorbic acid. In a further variation, the composition comprises 0.5 weight percent to 8.0 weight percent of the acid component and at least about 10 weight percent of the amphoteric surfactant. In a yet further variation of the composition, the composition comprises 3.0 weight percent of the acid component. The amphoteric surfactant, in one variation is selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant. In a further variation the composition includes 3.0 weight percent malic acid and at least about 10.0 weight percent of Cocamidopropyl Betaine surfactant.

In a further exemplary embodiment, a method for treating hair comprises the steps of applying a first composition to the hair to straighten the hair, rinsing the hair, allowing the hair to normalize, applying a second composition to the hair to remove residue left in the hair by the application of the first composition, the second composition having a pH of about 2.2. In one variation, the second composition includes an aqueous solution including an acid component and an amphoteric surfactant. The acid component, in one variation, includes at least one acid selected from the group of citric, salicylic, acetic, malic, and ascorbic acid. In a further variation, the composition comprises 0.5 weight percent to 8.0 weight percent of the acid component and at least about 10 weight percent of the amphoteric surfactant. The acid component, in a further variation, comprises 3.0 weight percent of the acid component. The amphoteric surfactant, in one variation, is selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant. In a yet further variation, the composition includes 3.0 weight percent malic acid and at least about 10.0 weight percent of Cocamidopropyl Betaine surfactant.

In a yet further exemplary embodiment, a method for treating hair comprises the steps of applying a first composition to the hair to straighten the hair, rinsing the hair, allowing the hair to normalize, applying a second composition to the hair to remove residue left in the hair by the application of the first composition, the second composition having a pH of about 2.2. In one variation, the hair is allowed to normalize by waiting at least 30 minutes between rinsing the hair and the application of the second composition. In another variation, the hair is allowed to normalize by waiting at least 4 hours between rinsing the hair and the application of the second composition. In a further variation, the hair is allowed to normalize by waiting at least 24 hours between rinsing the hair and the application of the second composition. In a yet further variation, the hair is allowed to normalize by waiting at least 48 hours between rinsing the hair and the application of the second composition.

In an exemplary composition for treating hair, the composition comprising an acidic component selected from the group of citric, salicylic, acetic, malic, and ascorbic acid and an amphoteric surfactant. The acidic component and the surfactant being incorporated with water to produce an aqueous solution having a pH of about 2.2. In one variation, the composition includes 0.5 weight percent to 8 weight percent of the acidic component. In one further variation, the composition includes 3 weight percent of the acidic component. The composition, in a yet further variation, includes 3 weight percent malic acid. The amphoteric surfactant, in one variation, is selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant. The amphoteric surfactant, in a further variation, comprises at least about 10 weight percent of the amphoteric surfactant. The amphoteric surfactant, in a yet further variation, comprises about 10 weight percent of Cocamidopropyl Betaine surfactant.

In another exemplary method for treating hair comprising the steps of treating the hair with an alkaline treatment, allowing the hair to normalize, and clarifying the hair with a hair clarifying treatment to remove a residue of the alkaline treatment from the hair. In one variation, the hair is allowed to normalize by waiting at least 30 minutes between the completion of the alkaline treatment and the commencement of the clarifying treatment. In another variation, the hair is allowed to normalize by waiting at least 4 hours between the completion of the alkaline treatment and the commencement of the clarifying treatment. In a further variation, the hair is allowed to normalize by waiting at least 24 hours between the completion of the alkaline treatment and the commencement of the clarifying treatment. In yet a further variation, the hair is allowed to normalize by waiting at least 48 hours between the completion of the alkaline treatment and the commencement of the clarifying treatment.

In yet another exemplary method for treating hair comprising the steps of treating the hair with an alkaline treatment, allowing the hair to normalize, and clarifying the hair with a hair clarifying treatment to remove a residue of the alkaline treatment from the hair. In one variation, the hair clarifying treatment includes the step of applying a composition to the hair, the composition comprising an aqueous solution including an acid component and an amphoteric surfactant. The acid component, in one variation, includes at least one acid selected from the group of citric, salicylic, acetic, malic, and ascorbic acid. In a further variation, the composition comprises 0.5 weight percent to 8.0 weight percent of the acid component and at least about 10 weight percent of the amphoteric surfactant. In a yet further variation, the composition comprises 3.0 weight percent of the acid component. The amphoteric surfactant, in one variation, is selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant. In another variation, the composition includes 3.0 weight percent malic acid and at least about 10.0 weight percent of Cocamidopropyl Betaine surfactant.

In an additional exemplary method for treating hair comprises the steps of applying a first composition to the hair, the first composition being an alkaline composition, rinsing the hair, allowing the hair to normalize, and applying a second composition to the hair to remove residue left in the hair by the application of the first composition. The second composition having a pH of about 2.2. The second composition, in one variation, includes an aqueous solution including an acid component and an amphoteric surfactant. The acid component, in one variation, includes at least one acid selected from the group of citric, salicylic, acetic, malic, and ascorbic acid. In a variation of the composition, the composition comprises 0.5 weight percent to 8.0 weight percent of the acid component and at least about 10 weight percent of the amphoteric surfactant. In a further variation of the composition, the composition comprises 3.0 weight percent of the acid component. The amphoteric surfactant, in another variation, is selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant. In a yet further variation, the composition includes 3.0 weight percent malic acid and at least about 10.0 weight percent of Cocamidopropyl Betaine surfactant.

DETAILED DESCRIPTION OF PREFERRED EMBODIMENTS

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Hair fibers include proteins and fatty acids and exhibit a baseline pH of around 4.0 to 6.0. Hair straightening treatments and permanent wave treatments alter the chemical bonds in hair fibers and hence the appearance of the hair fibers in part by reacting various compositions with the hair fibers at elevated pHs from the baseline pH of hair.

Hair that has been treated with a hair straightening treatment is chemically altered to have a straight appearance. At minimum a commercial hair straightening treatment includes applying to the hair a straightening composition having a pH of at least 12.0, which breaks the disulfide bonds in the hair fibers. During the hair straightening treatment the pH of the hair fibers is elevated from the baseline 4.0 to 6.0 to an elevated pH approaching the pH of the straightening composition.

Example hair straightening compositions include compositions of guanidine hydroxide, barium hydroxide, lithium hydroxide, sodium hydroxide, and potassium hydroxide, or mixtures thereof. U.S. Pat. No. 4,304,244 discloses a guanidine hydroxide composition used to straighten hair. Exemplary commercial embodiments of calcium hydroxide straightening compositions: Optimum Care available from Soft Sheen Products located in Chicago, Ill. 60619; Alternatives available from Soft Sheen Products located in Chicago, Ill. 60619; Motions available from Soft Sheen Products located in Chicago, Ill. 60619; Clairol Textures and Tones available from Clairol Inc Dist. located in Stamford, Conn. 06902; hair straightening compositions available from TCB located at Alberto Culver USA INC., Melrose Park, Ill. 60160; Realistic available from Revlon Professional Inc Dist in New York, N.Y. 10022; Fabulaxer available from Revlon Professional Inc Dist located in New York, N.Y. 10022; Creme Of Nature available from Revlon Professional Inc Dist, located in New York, N.Y. 10022; Dark and Lovely available from Carson Products Co. located in Savannah, Ga. 31403; PCJ available from Luster Products Inc. located in Chicago, Ill. 60609; Pink Conditioning Relaxer available from Luster Products Inc located in Chicago Ill. 60609; Soft & Beautiful available from Proline Corporation located in Dallas, Tex. 75212; Sheenique available from Summit Laboratories Inc. located in Chicago Heights, Ill. 60411; ISO Plus available from JM Products Inc. located at Po Box 4025 Little Rock, Ark. 72214-4025; Always Natural available from AP Products LTD located in New York, N.Y. 10801; and Ultra Sheen's Precise available from Johnson Products Co Inc. located in Chicago, Ill. 60620. A exemplary commercial embodiment of sodium hydroxide is Motions available from Soft Sheen located in Chicago, Ill. 60619.

The hair fibers remain at an elevated pH after the straightening composition has been rinsed from the hair and the hair straightening treatment has been completed. Over time, the pH of the hair fibers decreases, thereby normalizing the hair fibers. Eventually, the pH of the hair fibers returns to the baseline pH of 4.0 to 6.0.

Hair that has been treated with a permanent wave treatment is chemically altered to have a wavy appearance. At minimum a commercial permanent wave treatment includes applying to the hair a permanent wave composition having a pH in the range of 9.0 to 9.5, which breaks the disulfide bonds in the hair fibers. During the permanent wave treatment, the pH of the hair fibers is elevated from the baseline pH of 4.0 to 6.0 to an elevated pH approaching the pH of the permanent wave composition.

The hair fibers remain at an elevated pH after the perm composition has been rinsed from the hair and the permanent wave treatment has been completed. Over time, the pH of the hair fibers decreases, thereby normalizing the hair fibers. Eventually, the pH of the hair fibers returns to the baseline pH of 4.0 to 6.0.

A side effect of both hair straightening and permanent wave treatments is that residue from the hair straightening composition and the permanent wave composition becomes lodged under the cuticle portion of the hair after the hair straightening treatment or the permanent wave treatment is completed. The residue causes the hair fibers to feel coarse and dry and to have a dull appearance. Additionally, the residue causes manageability problems when the hair is later styled.

Traditionally conditioning/clarifying treatments are applied to hair subsequent to a hair straightening treatment or a permanent wave treatment within a short time period of the completion of the hair straightening treatment or permanent wave treatment, usually less than 10 minutes. However, traditional conditioning/clarifying treatments are relatively weak, pH of 4.0 to 4.5. The residue from the hair straightening treatment or permanent wave treatment is not removed from the hair by traditional conditioning/clarifying treatments An exemplary hair clarifying composition of the present invention is configured to remove the residue left behind in the hair following a hair straightening treatment or the permanent wave treatment. The exemplary hair clarifying composition includes an acid component and an amphoteric surfactant. The acid component is selected from the group of citric acid, salicyclic acid, acetic acid, malic acid and ascorbic acid or any type of fruit based acid or combination of acids. Preferably the acid component is malic acid. Malic acid is available from Haarman and Reimer located at 300 North Street, Tetersboro, N.J. 07608. The amphoteric surfactant is selected from the group of Cocamidopropyl Betaine, lauramidopropyl betaine, cocoamidopropyl hydroxysultaine, cocoamphoglycinate, and lauroamphogly- ciante. Preferably, the amphoteric surfactant is Cocamidopropyl Betaine. Cocamidopropyl Betaine is available from McIntyre Group, Ltd. located at 24601 Governors Highway, University Park, Ill. 60466.

Unless otherwise indicated, throughout this application the weight percent of the acid component and the amphoteric surfactant is a percentage of the overall weight of the hair clarifying composition.

In another preferred variation of the exemplary hair clarifying composition, the hair clarifying composition is an aqueous solution that includes 0.50 weight percent to 8 weight percent of malic acid and about 10 weight percent of Cocamidopropyl Betaine surfactant. The preferred variation of the exemplary clarifying composition has a pH of about 2.2. In a further preferred variation of the exemplary hair clarifying composition, the hair clarifying composition is an aqueous solution that includes 1 weight percent to 8 weight percent of malic acid and about 10 weight percent of Cocamidopropyl Betaine surfactant. In a yet further preferred variation of the exemplary hair clarifying composition, the hair clarifying composition is an aqueous solution that includes 3 weight percent to 8 weight percent of malic acid and about 10 weight percent of Cocamidopropyl Betaine surfactant. In a most preferred variation of the exemplary hair clarifying composition, the hair clarifying composition is an aqueous solution that includes 3 weight percent of malic acid and about 10 weight percent of Cocamidopropyl Betaine surfactant.

The hair clarifying composition of the present invention has a relatively strong acidic pH of about 2.2. As such, when the hair clarifying composition is applied to the pH of the hair is lowered below the baseline pH of 4.0 to 6.0 to a value approaching the pH of the hair clarifying composition. When the hair clarifying composition is rinsed from the hair, the pH of the hair over time returns to the baseline pH of 4.0 to 6.0.

The hair clarifying composition, along with its positive effects on removing residue from the hair, works to realign the cuticle of the hair. The cuticle of the hair can become disoriented during daily activity and due to various hair treatments. The strong acidic value of the hair clarifying composition assists the realigning of the cuticle of the hair. As such, the hair has better light reflection properties and has increased combability among other desirable properties.

The present invention includes an exemplary method for treating hair, following a hair straightening treatment or a permanent wave treatment, that removes the residue left in the hair from the hair straightening treatment or the permanent wave treatment, increases the shininess and smoothness of the hair, and generally causes treated hair to appear more nature and to be more manageable. The exemplary method includes subsequent to a hair straightening or permanent wave treatment, allowing the hair to normalize for a period of time. As the hair is normalizing, the pH of the hair returns closer to the baseline pH of the hair prior to the hair straightening treatment or the permanent wave treatment. It is not required that the pH of the hair return completely to the baseline pH for the hair to be normalized, only that the pH of the hair returns to a value closer to the baseline pH.

Once the hair has normalized, the hair is treated with the exemplary clarifying composition described above or variations of the exemplary clarifying compositions. The exemplary clarifying composition comprising an aqueous solution of an acidic component and an amphoteric surfactant.

In a preferred method, the hair is treated with an exemplary clarifying composition at least 30 minutes after the completion of the hair straightening treatment or the permanent wave treatment. In a further preferred, method the hair is treated with the exemplary composition at least 4 hours after the completion of the hair straightening treatment or the permanent wave treatment. In yet a further preferred method, the hair is treated with the exemplary composition at least 24 hours after the completion of the hair straightening treatment or the permanent wave treatment. In a most preferred method, the hair is treated with the exemplary composition at least 48 hours after the completion of the hair straightening treatment or the permanent wave treatment.

Reference will now be made to specific examples of this exemplary embodiment using the compositions and processes above described. It is to be understood that the examples are provided to more completely describe preferred embodiments and that no limitation to the scope of the invention is intended thereby. The following hair straightening treatment was employed in the Examples, 1–20.

Hair Straightening Treatment Used in Examples 1–20

Each model's hair was treated with a hair straightening composition. The hair straightening composition is a guanidine hydroxide produced by mixing of calcium hydroxide and guanidine carbonate. As stated earlier, U.S. Pat. No. 4,304,244 discloses a guanidine hydroxide hair straightening composition. The guanidine hydroxide hair straightening composition used in Examples 1–20 has a lower concentration of guanidine hydroxide as compared to other commercially available straightener products. Each Example 1–20 uses a hair straightening composition, hereafter referred to as mixture one, which is 75% of the strength of similar commercially available hair straightening compositions or a second hair straightening composition, hereafter referred to as mixture two, which is 50% of the strength of similar commercially available hair straightening compositions.

In each example, either mixture one or mixture two was applied to the hair of the model, the application taking approximately twenty minutes. The straightening mixture was left on the hair of the model for an additional twenty minutes while the model was positioned under a hair dryer with a cap over the hair. The use of heat assists the reaction of the guanidine carbonate and calcium hydroxide.

The hair was subsequently shampooed twice with a neutralizing shampoo and rinsed thoroughly. A thermal conditioning treatment was applied to the hair and the model was placed under the dryer for about five minutes. The thermal conditioning treatment includes a cationic agent and proteins. The thermal conditioning treatment adds moisture to the hair and assists in detangling the hair.

The hair was rinsed following the thermal conditioning treatment. Detangling spray was applied to the hair of the model and the hair was combed with a wide tooth comb. The model was placed under the hood dryer until the hair was damp to dry. The model was advised not to shampoo hair before his/her return appointment for the hair clarifying treatment of the present invention.

Clarifying Treatment Subsequent to Straightening Treatment Used in Examples 1–20

Each model's hair is inspected to determine a baseline for the amount of residue left in the hair as a result of the straightening treatment discussed above. The hair of the model is then wetted. An exemplary clarifying treatment of present invention is applied to the hair of the model and left in the hair for about one minute. The hair was then rinsed. The hair is shampooed with a moisture infusing shampoo and rinsed. A moisture infusing conditioner is then applied to the hair and rinsed. A detangling spray is then applied to the hair and the hair is placed under a warm hair dryer to dry the hair. The hair of the model is then inspected to determine the effects of the clarifying treatment on the removal of residue, increase in shine, increase in smoothness and overall manageability.

In Examples 1–20, various exemplary clarifying compositions and methods of treating the hair of a model subsequent to a hair straightening treatment were investigated. Exemplary clarifying compositions including 0.5 weight percent to 8.0 weight percent malic acid and about 10 weight percent of Cocamidopropyl Betaine surfactant are tested. In particular exemplary compositions having about 10 weight percent of Cocamidopropyl Betaine surfactant and about 0.5 weight percent, about 3.0 weight percent or about 8.0 weight percent malic acid are tested. Exemplary methods tested include applying the exemplary clarifying compositions approximately directly after the completion of the hair straightening treatment, applying the exemplary clarifying composition about 30 minutes after the completion of the hair straightening treatment, applying the exemplary clarifying composition about 4 hours after the completion of the hair straightening treatment, applying the exemplary clarifying composition about 24 hours after the completion of the hair straightening treatment, and applying the exemplary clarifying composition about 48 hours after the completion of the hair straightening treatment.

EXAMPLE 1

TABLE 1

| Hair Characteristics before Straightening Treatment and Clarifying Treatment | |
|---|---|
| Characteristic | Subject |
| Texture | Coarse |
| Density | Thick/Dense |
| Curl pattern | Wavy/Curly |
| Length | Beyond Shoulder |
| Color-treated | Highlighted 20% |
| Percentage of gray hair | None |
| Prior straightening treatments | None |
| Additional notes | None |

The model's hair was straightened with hair straightening mixture two. The hair straightening mixture was applied to the hair of the model, the application taking approximately ten minutes. The straightening mixture was left on the hair of the model for an additional ten minutes while the model was positioned under a hair dryer with a cap over the hair.

Thirty minutes subsequent to the hair straightening treatment, one side of the model's hair was clarified with a clarifying composition including 0.5 weight percent malic acid and 10.0 weight percent Cocamidopropyl Betaine surfactant. The stylist reported that the side of the hair that received the clarifying treatment had a softer feel than the untreated side of hair.

The model returned to the salon approximately five days after the clarifying treatment was administered for a follow-up evaluation. The stylist reported that the treated hair was more comb-able and less frizzy than the untreated side.

EXAMPLE 2

TABLE 2

Hair Characteristics before Straightening Treatment and Clarifying Treatment

| Characteristic | Subject |
| --- | --- |
| Texture | Medium |
| Density | Normal |
| Curl pattern | Wavy/Curly |
| Length | Shoulder |
| Color-treated | None |
| Percentage of gray hair | None |
| Prior straightening treatments | Seventy-one day prior, see Example 14 |
| Additional notes | None |

The model's hair was straightened with hair straightening mixture two. Twenty-four hours subsequent to the hair straightening treatment, one side of the model's hair was clarified with a clarifying composition including 0.5 weight percent malic acid and 10.0 weight percent Cocamidopropyl Betaine surfactant. The stylist reported that there was no significant difference between the treated side of the hair and the untreated side of the hair.

The model returned to the salon approximately four days after the clarifying treatment was administered for a follow-up evaluation. The stylist reported that there was still no significant difference between the treated side of the hair and the untreated side.

The model was then given a clarifying composition including 3.0 weight percent malic acid and 10.0 weight percent Cocamidopropyl Betaine to use on her hair. The model applied the 3.0 malic acid clarifying composition to her hair for approximately one minute and returned the following day for inspection of her hair. The 3.0 malic acid clarifying composition was applied to the models hair approximately 72 hours subsequent to the hair straightening treatment. The stylist reported that the hair appeared to be totally free of all residue from the hair straightening treatment and that the hair had increased softness and shine. The model could not believe the difference in her hair following the treatment with the 3.0 malic acid clarifying composition. Also, Compare Example 14, wherein the same model was tested with a clarifying composition including 3.0 weight percent malic acid and 10.0 weight percent Cocamidopropyl Betaine surfactant approximately 48 hours subsequent to the hair straightening treatment.

EXAMPLE 3

TABLE 3

Hair Characteristics before Straightening Treatment and Clarifying Treatment

| Characteristic | Subject |
| --- | --- |
| Texture | Coarse |
| Density | Thick/Dense |
| Curl pattern | Wavy/Curly |
| Length | Beyond Shoulder |
| Color-treated | None |
| Percentage of gray hair | 20% |
| Prior straightening treatments | None |
| Additional notes | None |

The model's hair was straightened with hair straightening mixture one. Forty-eight hours subsequent to the hair straightening treatment, one side of the model's hair was clarified with a clarifying composition including 0.5 weight percent malic acid and 10.0 weight percent Cocamidopropyl Betaine surfactant. The stylist reported that the treated side of the hair combed and detangled better than the untreated side, had increased smoothness over the untreated side, and was in overall better condition than the untreated side.

The model returned to the salon approximately six days after the clarifying treatment was administered for a follow-up evaluation. The stylist reported that the treated side still exhibited better characteristics than the untreated side.

EXAMPLE 4

TABLE 4

Hair Characteristics before Straightening Treatment and Clarifying Treatment

| Characteristic | Subject |
| --- | --- |
| Texture | Fine |
| Density | Thick/dense |
| Curl pattern | Tightly curly |
| Length | Beyond shoulder |
| Color-treated | None |
| Percentage of gray hair | None |
| Prior straightening treatments | None |
| Additional notes | Blonde hair |

The model's hair was straightened with hair straightening mixture one. Directly following the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that initially the treated hair felt very soft and smooth, but as the hair dried it became more gritty and perceptively dry. The model returned to the salon after two days for a follow-up evaluation. The stylist reported that the treated side of model's hair reverted more than the untreated side. Further, there was not a dramatic difference in the condition of the treated side versus the untreated side. The hair in general still felt dry and gritty. The model also reported some soreness on her scalp.

EXAMPLE 5

TABLE 5

Hair Characteristics before Straightening Treatment and Clarifying Treatment

| Characteristic | Subject |
| --- | --- |
| Texture | Fine |
| Density | Thin |
| Curl pattern | Slightly Wavy |
| Length | Shoulder |
| Color-treated | Permanent |
| Percentage of gray hair | Up to 20 Percent |
| Prior straightening treatments | None |
| Additional notes | None |

The model's hair was straightened with hair straightening mixture two. Directly following the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that initially the treated hair felt very soft and smooth, but as the hair dried it became more gritty and perceptively dry. The model returned to the salon after two days for a follow-up evaluation. The stylist reported similar straightness on both the treated and untreated sides; both sides were as straight as the day of service, no reversion. Further, the hair in general still felt dry and gritty. The model also exhibited some soreness on her scalp.

EXAMPLE 6

TABLE 6

Hair Characteristics before Straightening Treatment and Clarifying Treatment

| Characteristic | Subject |
| --- | --- |
| Texture | Medium |
| Density | Normal |
| Curl pattern | Slightly Wavy |
| Length | Beyond shoulder |
| Color-treated | None |
| Percentage of gray hair | Up to 20 Percent |
| Prior straightening treatments | None |
| Additional notes | None |

The model's hair was straightened with hair straightening mixture one. Directly following the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that initially the treated hair felt very soft and smooth, but as the hair dried it became more gritty and perceptively dry. The model returned to the salon after two days for a follow-up evaluation. The stylist reported that both sides of the model's hair exhibited similar straightness on both the treated and untreated sides; both sides were as straight as the day of service, no reversion. Further, the hair in general still felt dry and gritty. The model had no scalp irritation. The model commented that she was thrilled with her hair and that she was willing to live with the dry feeling to have straight hair.

EXAMPLE 7

TABLE 7

Hair Characteristics before Straightening Treatment and Clarifying Treatment

| Characteristic | Subject |
| --- | --- |
| Texture | Coarse |
| Density | Thick/Dense |
| Curl pattern | Tightly Curly |
| Length | Beyond shoulder |
| Color-treated | None |
| Percentage of gray hair | None |
| Prior straightening treatments | None |
| Additional notes | Red Hair |

The model's hair was straightened with hair straightening mixture one. Directly following the hair straightening treatment, the entire head of hair was clarified with a clarifying composition including 3.0 weight percent malic acid and 10.0 weight percent Cocamidopropyl Betaine surfactant.

The stylist reported directly following the clarifying treatment that initially the treated hair felt very soft and smooth, but as the hair dried it became more gritty and perceptively dry. The model returned to the salon after two days for a follow-up evaluation. The stylist reported that the model's hair exhibited no reversion, but that in general still felt dry and gritty.

EXAMPLE 8

TABLE 8

Hair Characteristics before Straightening Treatment and Clarifying Treatment

| Characteristic | Subject |
| --- | --- |
| Texture | Medium |
| Density | Normal |
| Curl pattern | Wavy/Curly |
| Length | Shoulder |
| Color-treated | Permanent |
| Percentage of gray hair | None |
| Prior straightening treatments | None |
| Additional notes | None |

The model's hair was straightened with hair straightening mixture two. Thirty minutes subsequent to the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that the treated hair had increased smoothness over the untreated side. The model returned to the salon after three days for a follow-up evaluation. The stylist reported that the treated side had increased smoothness and increased shine over the untreated side. Further, there was some evidence of curl reversion on the treated hair and that the treated hair had increased frizziness.

EXAMPLE 9

TABLE 9

Hair Characteristics before Straightening Treatment and Clarifying Treatment

| Characteristic | Subject |
| --- | --- |
| Texture | Medium |
| Density | Thick/Dense |
| Curl pattern | Slightly Wavy |
| Length | Beyond Shoulder |
| Color-treated | Permanent and Bleached |
| Percentage of gray hair | None |
| Prior straightening treatments | Nine Months |
| Additional notes | None |

The model's hair was straightened with hair straightening mixture two. Four hours subsequent to the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that the treated hair had increased smoothness over the untreated side and was more tangle free. The model returned to the salon after three days for a follow-up evaluation. The stylist reported that the treated side had increased smoothness and increased shine over the untreated side. Further, the treated side was noticeably more frizzy than the untreated side and there was some reversion.

EXAMPLE 10

TABLE 10

Hair Characteristics before Straightening Treatment and Clarifying Treatment

| Characteristic | Subject |
| --- | --- |
| Texture | Fine |
| Density | Normal |
| Curl pattern | Wavy/Curly |
| Length | Shoulder |
| Color-treated | Highlighted 10% |
| Percentage of gray hair | 0% |
| Prior straightening treatments | None |
| Additional notes | None |

The model's hair was straightened with hair straightening mixture two. Twenty-four hours subsequent to the hair straightening treatment, one side of the model's hair was clarified with a clarifying composition including 3.0 weight percent malic acid and 10.0 weight percent Cocamidopropyl Betaine surfactant.

The stylist reported directly following the clarifying treatment that the treated hair had increased smoothness and increased shine over the untreated side. Further, the treated side was more comb-able than the untreated side. The model returned to the salon after two days for a follow-up evaluation. The stylist reported that the treated side had increased smoothness and increased shine over the untreated side. Further, there was some evidence of minor curl reversion on the treated hair, but the treated hair was in overall good condition. The stylist reported that the results of this test are in line with the results of Examples 11–16.

EXAMPLE 11

TABLE 11

Hair Characteristics before Straightening Treatment and Clarifying Treatment

| Characteristic | Subject |
| --- | --- |
| Texture | Fine |
| Density | Normal |
| Curl pattern | Wavy/Curly |
| Length | Beyond shoulder |
| Color-treated | High Lift |
| Percentage of gray hair | None |
| Prior straightening treatments | None |
| Additional notes | Recent use of Sun-In product |

The model's hair was straightened with hair straightening mixture two. After completing the hair straightening treatment, the stylist noted the dry, coarse feel typically associated with hydroxide residual. Forty-eight hours subsequent to the hair straightening treatment, the entire head of hair of the model was clarified with a clarifying composition including 3.0 weight percent malic acid and 10.0 weight percent Cocamidopropyl Betaine surfactant.

The stylist reported directly following the clarifying treatment that the treated hair exhibited increased softness, increased shine and increased smoothness. Further, the hair exhibited no noticeable reversion, frizziness or hydroxide residue. The model returned to the salon in two days for a follow-up evaluation. No scalp irritation was observed. The hair exhibited a healthy feeling, was shiny, and was soft.

EXAMPLE 12

TABLE 12

Hair Characteristics before Straightening Treatment and Clarifying Treatment

| Characteristic | Subject |
| --- | --- |
| Texture | Fine |
| Density | Thick/Dense |
| Curl pattern | Wavy/Curly |
| Length | Above shoulder |
| Color-treated | None |
| Percentage of gray hair | None |
| Prior straightening treatments | Fourteen days prior, Example 4 |
| Additional notes | None |

The model's hair was straightened with hair straightening mixture two. Forty-eight hours subsequent to the hair straightening treatment, the entire head of hair of the model was clarified with a clarifying composition including 3.0 weight percent malic acid and 10.0 weight percent Cocamidopropyl Betaine surfactant.

The model returned to the salon in two days for a follow-up evaluation. No scalp irritation was observed. The hair exhibited no noticeable reversion. Further, the gritty feeling due to the hydroxide residue was gone. The hair exhibited a healthy feeling, was shiny, and was soft. The model was extremely satisfied with the results.

EXAMPLE 13

TABLE 13

Hair Characteristics before Straightening Treatment and Clarifying Treatment

| Characteristic | Subject |
| --- | --- |
| Texture | Coarse |
| Density | Thick |
| Curl pattern | Wavy/Curly |
| Length | Shoulder |
| Color-treated | None |
| Percentage of gray hair | None |
| Prior straightening treatments | Sixteen days prior, Example 7 |
| Additional notes | None |

The model's hair was straightened with hair straightening mixture two. The model was provided with a clarifying composition including 3.0 weight percent malic acid and 10.0 weight percent Cocamidopropyl Betaine surfactant to be used at home forty-eight hours subsequent to the hair straightening treatment.

The model communicated that the clarifying composition worked very well. Her hair feels very soft and smooth. The model was extremely satisfied with the results.

EXAMPLE 14

TABLE 14

| Hair Characteristics before Straightening Treatment and Clarifying Treatment | |
|---|---|
| Characteristic | Subject |
| Texture | Medium |
| Density | Normal |
| Curl pattern | Wavy/Curly |
| Length | Shoulder |
| Color-treated | None |
| Percentage of gray hair | None |
| Prior straightening treatments | Forty-three days prior |
| Additional notes | None |

The model's hair was straightened with hair straightening mixture two. Forty-eight hours subsequent to the hair straightening treatment, the entire head of hair of the model was clarified with a clarifying composition including 3.0 weight percent malic acid and 10.0 weight percent Cocamidopropyl Betaine surfactant.

The model returned to the salon after two days for a follow-up evaluation. No scalp irritation was observed. The hair exhibited no noticeable reversion. Further, the gritty feeling due to the hydroxide residue was gone. The hair exhibited a healthy feeling, was shiny, and was soft. The model stated that her hair never felt in such good condition.

EXAMPLE 15

TABLE 15

| Hair Characteristics before Straightening Treatment and Clarifying Treatment | |
|---|---|
| Characteristic | Subject |
| Texture | Fine |
| Density | Normal |
| Curl pattern | Slightly Wavy |
| Length | Shoulder |
| Color-treated | None |
| Percentage of gray hair | Up to 20% |
| Prior straightening treatments | None |
| Additional notes | None |

The model's hair was straightened with hair straightening mixture one. Forty-eight hours subsequent to the hair straightening treatment, the entire head of hair of the model was clarified with a clarifying composition including 3.0 weight percent malic acid and 10.0 weight percent Cocamidopropyl Betaine surfactant.

The model returned to the salon after two days for a follow-up evaluation. No scalp irritation was observed. The hair exhibited no noticeable reversion. Further, the gritty feeling due to the hydroxide residue was gone. The hair exhibited a healthy feeling, was shiny, and was soft. The model was very satisfied.

EXAMPLE 16

TABLE 16

| Hair Characteristics before Straightening Treatment and Clarifying Treatment | |
|---|---|
| Characteristic | Subject |
| Texture | Medium |
| Density | Normal |
| Curl pattern | Wavy/Curly |
| Length | Shoulder |
| Color-treated | None |
| Percentage of gray hair | None |
| Prior straightening treatments | None |
| Additional notes | None |

The model's hair was straightened with hair straightening mixture one. Forty-eight hours subsequent to the hair straightening treatment, the entire head of hair of the model was clarified with a clarifying composition including 3.0 weight percent malic acid and 10.0 weight percent Cocamidopropyl Betaine surfactant.

The model returned to the salon after two days for a follow-up evaluation. No scalp irritation was observed. The hair exhibited no noticeable reversion. Further, the gritty feeling due to the hydroxide residue was gone. The hair exhibited a healthy feeling, was shiny, and was soft. The model was extremely satisfied.

EXAMPLE 17

TABLE 17

| Hair Characteristics before Straightening Treatment and Clarifying Treatment | |
|---|---|
| Characteristic | Subject |
| Texture | Fine |
| Density | Thick/Dense |
| Curl pattern | Wavy/Curly |
| Length | Beyond Shoulder |
| Color-treated | Permanent Dye Application |
| Percentage of gray hair | Up to 20% |
| Prior straightening treatments | None |
| Additional notes | None |

The model's hair was straightened with hair straightening mixture two. Thirty minutes subsequent to the hair straightening treatment, one side of the model's hair was clarified with a clarifying composition including 8.0 weight percent malic acid and 10.0 weight percent Cocamidopropyl Betaine surfactant.

After the completion of the clarifying treatment, the stylist noted that the treated hair had increased shine compared to the untreated side. However, there was noticeable reversion in the treated side. The model returned to the salon after two days for a follow-up evaluation. The stylist noted that the treated hair showed definite curl reversion and that there was a loss of color from a previous hair dye application.

EXAMPLE 18

TABLE 18

| Hair Characteristics before Straightening Treatment and Clarifying Treatment | |
|---|---|
| Characteristic | Subject |
| Texture | Fine |
| Density | Normal |
| Curl pattern | Wavy/Curly |
| Length | Beyond Shoulder |
| Color-treated | Permanent Dye Application |
| Percentage of gray hair | Up to 20% |
| Prior straightening treatments | None |
| Additional notes | None |

The model's hair was straightened with hair straightening mixture two. Four hours subsequent to the hair straightening treatment, one side of the model's hair was clarified with a clarifying composition including 8.0 weight percent malic acid and 10.0 weight percent Cocamidopropyl Betaine surfactant.

After the completion of the clarifying treatment, the stylist noted that the treated hair showed very evident signs of curl reversion and some loss of color from a previous permanent hair dye application. The model returned to the salon after two days for follow-up a evaluation. The stylist noted that the treated hair was in generally good condition but the treated hair still showed definite curl reversion as compared to the untreated side.

EXAMPLE 19

TABLE 19

| Hair Characteristics before Straightening Treatment and Clarifying Treatment | |
|---|---|
| Characteristic | Subject |
| Texture | Fine |
| Density | Normal |
| Curl pattern | Wavy/Curly |
| Length | Above Shoulder |
| Color-treated | Permanent |
| Percentage of gray hair | None |
| Prior straightening treatments | None |
| Additional notes | None |

The model's hair was straightened with hair straightening mixture two. Twenty-four hours subsequent to the hair straightening treatment, one side of the model's hair was clarified with a clarifying composition including 8.0 weight percent malic acid and 10.0 weight percent Cocamidopropyl Betaine surfactant.

After the completion of the clarifying treatment, the stylist noted that the treated hair was noticeably drier and frizzier compared to the untreated side. The model returned to the salon after five days for a follow-up evaluation. The stylist noted that the treated hair had increased smoothness and increased shine compared to the untreated side.

EXAMPLE 20

TABLE 20

| Hair Characteristics before Straightening Treatment and Clarifying Treatment | |
|---|---|
| Characteristic | Subject |
| Texture | Medium |
| Density | Thick/Dense |
| Curl pattern | Wavy/Curly |
| Length | Beyond Shoulder |
| Color-treated | Permanent |
| Percentage of gray hair | None |
| Prior straightening treatments | None |
| Additional notes | None |

The model's hair was straightened with hair straightening mixture two. Forty-eight hours subsequent to the hair straightening treatment, one side of the model's hair was clarified with a clarifying composition including 8.0 weight percent malic acid and 10.0 weight percent Cocamidopropyl Betaine surfactant.

After the completion of the clarifying treatment, the stylist noted that the treated hair noticeably had increased softness and increased shine. Further, the treated hair was easier to comb and detangle compared to the untreated side. The model returned to the salon after five days for follow-up evaluation. The stylist noted that the treated hair still had noticeable increased softness and increased shine compared to the untreated side. Further, there was no indication of reversion. The hair did suffer a depletion of permanent hair color.

Based upon the results of Examples 1–20, it was observed that hair clarifying compositions including 10 weight percent of Cocamidopropyl Betaine surfactant and 0.5 weight percent to 8 weight percent malic acid has some benefit to removing residue from hair that has been subjected to a hair straightening treatment. It was further observed that 3 weight percent to 8 weight percent of malic acid, produced substantially better results concerning the removal of residue from the hair thereby increasing smoothness and shine. It was yet further observed that at 8 weight percent malic acid, the hair clarifying composition lifted color from the hair. As such, based on the observation in Examples 1–20, it is preferred to clarify hair subsequent to a hair straightening treatment with a clarifying composition including 10 weight percent Cocamidopropyl Betaine surfactant and 3 weight percent malic acid.

Further based upon the results of Examples 1–20, it was observed that the hair needs to be allowed to normalize between the hair straightening treatment and the clarifying treatment for two reasons. First, using the clarifying treatment right after the straightening treatment reduces the effectiveness of the residue removal. Second, because the internal bond structure of the hair has not been allowed to strengthen, by normalizing, the clarifying treatment can cause reversion in the hair structure and increased frizzing. It was observed that the clarifying treatment should be commenced at least thirty minutes to forty-eight hours after the completion of the hair straightening treatment. It was further observed that the clarifying treatment should be commenced at least four hours to forty-eight hours after the completion of the hair straightening treatment. Based upon the results of Examples 1–20, it is preferred that the clarifying treatment should be commenced at least twenty-four hours to forty-eight hours after the completion of the hair straightening treatment. As such, it is within the scope of the present invention, that the clarifying treatment will be commenced at times beyond forty-eight hours, such as seventy-two hours, ninety-six hours, one hundred twenty hours or other times.

The hair clarifying composition of the present invention may also be used to remove residue from hair that has not been treated with a hair straightening treatment or a permanent wave treatment. Often times, minerals in household water that is used in the shampooing and rinsing of hair are left behind when the hair is rinsed. Additionally, residue can be left in hair due to natural perspiration.

Reference will now be made to specific examples of this exemplary embodiment using the hair clarifying compositions to remove residue from hair that has not been treated with a hair straightening treatment or a permanent wave treatment. It is to be understood that the examples are provided to more completely describe preferred embodiments and that no limitation to the scope of the invention is intended thereby.

In Examples 21 and 22, an exemplary clarifying treatment of present invention is applied to the hair of the model and left in the hair for about one minute. The hair was then rinsed. In particular exemplary compositions having about 10 weight percent of Cocamidopropyl Betaine surfactant and about 3.0 weight percent malic acid were tested. However, it is within the scope of the invention to use clarifying compositions including 0.5 weight percent to 8.0 weight percent malic acid and about 10 weight percent of Cocamidopropyl Betaine surfactant.

EXAMPLE 21

The hair of the model was clarified with a clarifying composition including 3.0 weight percent malic acid and 10.0 weight percent Cocamidopropyl Betaine surfactant. The model used the clarifying composition two to three times a week for a couple of months. The model noted that the clarifying composition brightened her blond hair and highlights. Additionally, the clarifying composition removed the residue from her hair. The clarifying composition had a detangling effect and a conditioning effect on the model's hair. The model further noted that her hair was more manageable, easier to style and the style appeared to last longer.

EXAMPLE 22

The model has very long straight hair that tended to kink and frizz at the ends. The model has also had a problem with breakage and dullness. After using the clarifying composition of 3.0 weight percent malic acid and 10.0 weight percent Cocamidopropyl Betaine surfactant, the model noted that her hair has a smooth, healthy look and increased shine.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

I claim:

1. A method for increasing the manageability of hair having a baseline pH of around 4.0 to 6.0, the method comprising the steps of:

applying an alkaline composition selected from the group consisting of guanidine hydroxide, barium hydroxide, lithium hydroxide, sodium hydroxide, and potassium hydroxide to the hair such that the pH of the hair is elevated above the baseline pH of 4.0 to 6.0;

heating the hair while the alkaline composition is applied to the hair, the alkaline composition having a pH of at least 12;

shampooing and rinsing the alkaline composition from the hair;

allowing the pH of the hair to return towards the baseline pH of around 4.0 to 6.0 by waiting at least 30 minutes between the rinsing of the hair and the application of an acidic composition to the hair;

applying the acidic composition to the hair such that the pH of the hair is reduced below the baseline pH of 4.0 to 6.0, the acidic composition including an acid component and a surfactant; and rinsing the hair, the resultant hair having increased manageability.

2. The method of claim 1, wherein the alkaline composition is in contact with the hair during the steps of applying the alkaline composition and heating the hair combined for a duration of at least approximately twenty minutes to approximately forty minutes.

3. The method of claim 2, wherein the step of applying the alkaline composition has an associated application time of approximately ten minutes to approximately twenty minutes.

4. The method of claim 3, wherein the heating step has an associated heating time of approximately ten minutes to approximately twenty minutes.

5. The method of claim 3, wherein the hair is allowed to return towards the baseline pH of around 4.0 to 6.0 by waiting at least 4 hours between rinsing the hair and the application of the acidic composition.

6. The method of claim 5, wherein the hair is allowed to return towards the baseline pH of around 4.0 to 6.0 by waiting at least 24 hours between rinsing the hair and the application of the acidic composition.

7. The method of claim 6, wherein the hair is allowed to return towards the baseline pH of around 4.0 to 6.0 by waiting at least 48 hours between rinsing the hair and the application of the acidic composition.

8. The method of claim 1, wherein the acidic composition has a pH of about 2.2.

9. The method of claim 8, wherein the acid component is selected from the group of citric, salicylic, acetic, malic, and ascorbic acid and the surfactant is an amphoteric surfactant selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant.

10. The method of claim 3, wherein the alkaline composition is guadinine hydroxide, the acid composition includes about 3 weight percent malic acid and about 10 weight percent Cocamidopropyl Betaine.

11. The method of claim 10, wherein the hair is allowed to return towards the baseline pH of around 4.0 to 6.0 by waiting at least 4 hours between rinsing the hair and the application of the acidic composition.

12. The method of claim 11, wherein the hair is allowed to return towards the baseline pH of around 4.0 to 6.0 by waiting at least 24 hours between rinsing the hair and the application of the acidic composition.

13. The method of claim 12, wherein the hair is allowed to return towards the baseline pH of around 4.0 to 6.0 by waiting at least 48 hours between rinsing the hair and the application of the acidic composition.

14. A hair treatment system for increasing the manageability of the hair, the hair having a baseline pH of about 4.0 to about 6.0, the hair treatment system comprising:
   an alkaline composition which raises the pH of the hair above the baseline pH, the first alkaline composition to be applied to the hair and to remain in contact with the hair throughout an application of heat to the hair and subsequently rinsed from the hair, wherein the alkaline composition is selected from the group consisting of guanidine hydroxide, barium hydroxide, lithium hydroxide, sodium hydroxide, and potassium hydroxide; and
   an acidic composition having a pH of about 2.2, the acidic composition to be applied to the hair subsequent to the rinsing of the first alkaline composition and subsequent to a time period of at least 30 minutes such that the pH of the hair returns towards the baseline pH of 4.0 to 6.0 before application of the acidic component.

15. The hair treatment system of claim 14, wherein the wherein the alkaline composition is to be in contact with the hair for a duration of at least approximately twenty minutes to approximately forty minutes.

16. The hair treatment system of claim 15, wherein the application of the alkaline composition has an associated application time of approximately ten minutes to approximately twenty minutes.

17. The hair treatment system of claim 16, wherein heat is to be applied to the hair for an associated heating time of approximately ten minutes to approximately twenty minutes.

18. The hair treatment system of claim 14, wherein the alkaline composition has a pH of at least 12.

19. The hair treatment system of claim 14, wherein the acidic composition includes an acid component selected from the group of citric, salicylic, acetic, malic, and ascorbic acid and an amphoteric surfactant selected from the group of Cocamidopropyl Betaine surfactant, Lauramidopropyl Betaine surfactant, Cocamidopropyl Hydroxysultaine surfactant, Cocoamphoglycinate surfactant, and Lauroamphoglycinate surfactant.

20. The hair treatment system of claim 18, wherein the acidic composition includes about 3 weight percent to about 8 weight percent of the acid component.

21. The hair treatment system of claim 20, wherein the acidic composition includes about 3.0 weight percent of malic acid and about 10.0 weight percent of Cocamidopropyl Betaine.

22. The hair treatment system of claim 14, further comprising a thermal conditioning composition configured to add moisture to the hair and to be applied to the hair between the alkaline composition and the acidic composition, the thermal conditioning composition including a cationic agent and proteins.

23. The hair treatment system of claim 22, further comprising a neutralizing shampoo to applied subsequent to the alkaline composition and prior to the thermal conditioning treatment.

24. The hair treatment system of claim 15, wherein the hair is allowed to return towards the baseline pH of around 4.0 to 6.0 by waiting at least 4 hours between rinsing the hair and the application of the acidic composition.

25. The hair treatment system of claim 24, wherein the hair is allowed to return towards the baseline pH of around 4.0 to 6.0 by waiting at least 24 hours between rinsing the hair and the application of the acidic composition.

26. The hair treatment system of claim 25, wherein the hair is allowed to return towards the baseline pH of around 4.0 to 6.0 by waiting at least 48 hours between rinsing the hair and the application of the acidic composition.

27. A hair treatment system for increasing the manageability of the hair the hair treatment system comprising:
   a hydroxide composition to be applied to the hair and to remain in contact with the hair throughout an application of heat to the hair and subsequently rinsed from the hair, the hydroxide composition remaining in contact with the hair for a duration of at least approximately twenty minutes to approximately forty minutes, wherein the hydroxide composition is a guanidine hydroxide composition formed by the mixing of a calcium hydroxide composition and a guanidine carbonate composition; and
   an acidic composition having a pH of about 2.2 to be applied to the hair at least 30 minutes subsequent to rinsing the hydroxide composition from the hair, the acidic composition including an acid component selected from the group of citric, salicylic, acetic, malic, and ascorbic acid and an amphoteric surfactant selected from the group of Cocamidopropyl Betaine surfactant, Lauramidopropyl Betaine surfactant, Cocoamidopropyl Hydroxysultaine surfactant, Cocoamphoglycinate surfactant, and Lauroamphoglycinate surfactant.

28. The hair treatment system of claim 27, wherein the acidic composition includes about 3.0 weight percent of the acid component to about 8.0 weight percent of the acid component.

29. The hair treatment system of claim 27, wherein the acidic component is applied to the hair at least 4 hours subsequent to rinsing the hydroxide composition from the hair.

30. The hair treatment system of claim 29, wherein the acidic component is applied to the hair at least 24 hours subsequent to rinsing the hydroxide composition from the hair.

31. The hair treatment system of claim 30, wherein the acidic component is applied to the hair at least 48 hours subsequent to rinsing the hydroxide composition from the hair.

* * * * *